United States Patent
Yen

(10) Patent No.: US 12,343,090 B2
(45) Date of Patent: Jul. 1, 2025

(54) NAVIGATION METHOD AND NAVIGATION SYSTEM FOR SURGICAL INSTRUMENT

(71) Applicant: Point Robotics Medtech Inc., Hsinchu County (TW)

(72) Inventor: Chia-Ho Yen, Hsinchu County (TW)

(73) Assignee: POINT ROBOTICS (SINGAPORE) PTE. LTD., Singapore (SG)

( * ) Notice: Subject to any disclaimer, the term of this patent is extended or adjusted under 35 U.S.C. 154(b) by 604 days.

(21) Appl. No.: 17/879,742

(22) Filed: Aug. 2, 2022

(65) Prior Publication Data
US 2023/0310087 A1 Oct. 5, 2023

(51) Int. Cl.
*A61B 34/20* (2016.01)
*A61B 34/10* (2016.01)
*A61B 34/30* (2016.01)

(52) U.S. Cl.
CPC .............. *A61B 34/20* (2016.02); *A61B 34/30* (2016.02); *A61B 2034/107* (2016.02); *A61B 2034/2055* (2016.02)

(58) Field of Classification Search
CPC ......... A61B 34/00; A61B 34/10; A61B 34/20; A61B 34/30; A61B 34/32; A61B 34/37; A61B 2034/107; A61B 2034/2055; A61B 2034/2048; A61B 2034/2051; A61B 2034/2061
See application file for complete search history.

(56) References Cited

U.S. PATENT DOCUMENTS

| | | | |
|---|---|---|---|
| 2015/0182285 A1* | 7/2015 | Yen | A61B 17/1626 606/86 R |
| 2021/0196397 A1 | 7/2021 | Peng et al. | |
| 2021/0322043 A1 | 10/2021 | Suzuki | |

FOREIGN PATENT DOCUMENTS

| | | |
|---|---|---|
| CN | 111035454 A | 4/2020 |
| CN | 112057141 A | 12/2020 |
| CN | 112370167 A | 2/2021 |
| CN | 112804962 A | 5/2021 |

* cited by examiner

*Primary Examiner* — Boniface N Nganga
(74) *Attorney, Agent, or Firm* — Li & Cai Intellectual Property Office

(57) ABSTRACT

A navigation method and a navigation system for a surgical instrument are provided. The navigation method includes: setting a predetermined surgical path; measuring a position and an orientation of the surgical instrument through a positioning unit, in which the surgical instrument has a transmission mechanism and an operating end; measuring a stress condition of the operating end of the surgical instrument by a force sensor; calculating first deformation information, induced due to the stress condition, of the surgical instrument according to a force deformation model; calculating a compensation amount according to the first deformation information and the measured position and orientation of the surgical instrument; and adjusting the surgical instrument to a new position or orientation according to the compensation amount, so as to maintain the surgical instrument on the predetermined surgical path.

16 Claims, 8 Drawing Sheets

NAVIGATION METHOD AND NAVIGATION SYSTEM FOR SURGICAL INSTRUMENT

CROSS-REFERENCE TO RELATED PATENT APPLICATION

This application claims the benefit of priority to Taiwan Patent Application No. 111112381, filed on Mar. 31, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a navigation method and a navigation system for a surgical instrument, and more particularly to a navigation method and a navigation system which are capable of correcting a path according to a deviation of the surgical instrument being deformed by force.

BACKGROUND OF THE DISCLOSURE

In a common orthopedic surgery, computer-assisted navigation software or an image-guided robotic arm is often used to assist in positioning during the surgery.

For example, optical tracking can be used to measure position and orientation of a robotic arm relative to an objective bone, and subtle positioning as well as the orthopedic surgery can be conducted through dynamically tracking compensation control. Specifically, the optical tracking can be performed by detecting reflective balls arranged on the robotic arm, so as to determine the position, orientation, speed and other information of the robotic arm relative to the patient.

However, in an orthopedic surgery in which a surgical instrument needs to extend even deeper into a surgical site, as a surgical end of the surgical instrument enters into the surgical site and thus is visually blocked, the surgical instrument may be affected by external forces, such as that from extrusion or hard objects, during the operation, which can lead to deformation of the surgical instrument. In circumstances where it is unable to know external forces and the extent the surgical instrument deforms, such deformation may lead to errors to computer-aided navigation, which may cause the surgical instrument to deviate from a predetermined surgical path and further increase the risk of surgical failure.

SUMMARY OF THE DISCLOSURE

In response to the above-referenced technical inadequacies, the present disclosure provides a navigation method and a navigation system that can perform path correction according to a deviation of a surgical instrument deformed by force.

In one aspect, the present disclosure provides a navigation method for a surgical instrument, and the method includes: setting a predetermined surgical path; measuring a position and an orientation of the surgical instrument through a positioning unit, wherein the surgical instrument has a transmission mechanism and an operating end; measuring a stress condition or a bending condition of the operating end of the surgical instrument by a sensor; calculating first deformation information, resulted by the stress condition, of the surgical instrument according to a force deformation model; calculating a compensation amount according to the first deformation information, the position and the orientation of the surgical instrument that are measured; and adjusting the surgical instrument to a new position or a new orientation according to the compensation amount, so as to maintain the surgical instrument on the predetermined surgical path.

In another aspect, the present disclosure provides a navigation system, which includes a computing device, a surgical instrument, and a driving mechanism. The computing device includes a processor and a memory. A sensor electrically connected to the computing device is disposed on the surgical instrument, and the surgical instrument has a transmission mechanism and an operating end. The driving mechanism is connected to the transmission mechanism and is controlled by the computing device to drive the surgical instrument. The processor is configured to: obtain a predetermined surgical path; measure a position and an orientation of the surgical instrument through a positioning unit; measure a stress condition or a bending condition of the operating end of the surgical instrument by a sensor; calculate first deformation information, resulted by the stress condition, of the surgical instrument according to a force deformation model; calculate a compensation amount according to the first deformation information and the position and the orientation of the surgical instrument that are measured; and adjust the surgical instrument to a new position or a new orientation according to the compensation amount, so as to maintain the surgical instrument on the predetermined surgical path.

One of advantages of the disclosure is that, in the disclosed navigation method and the navigation system for the surgical instrument, the deformation information of the surgical instrument can be measured and calculated in real time, the deviation of the surgical instrument can be calculated and corrected according to the deformation information during navigation. Also, the deviation of the surgical instrument can be displayed on a navigation interface and correspondingly compensated, which can improve an overall navigation accuracy.

In addition, in the disclosed navigation method and navigation system for the surgical instrument, force and temperature conditions of the surgical instrument can be monitored in real time during navigation, and if the exerted force exceeds a set range, the user is reminded of potential breakage of the surgical instrument, or a corresponding risk control process is executed.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
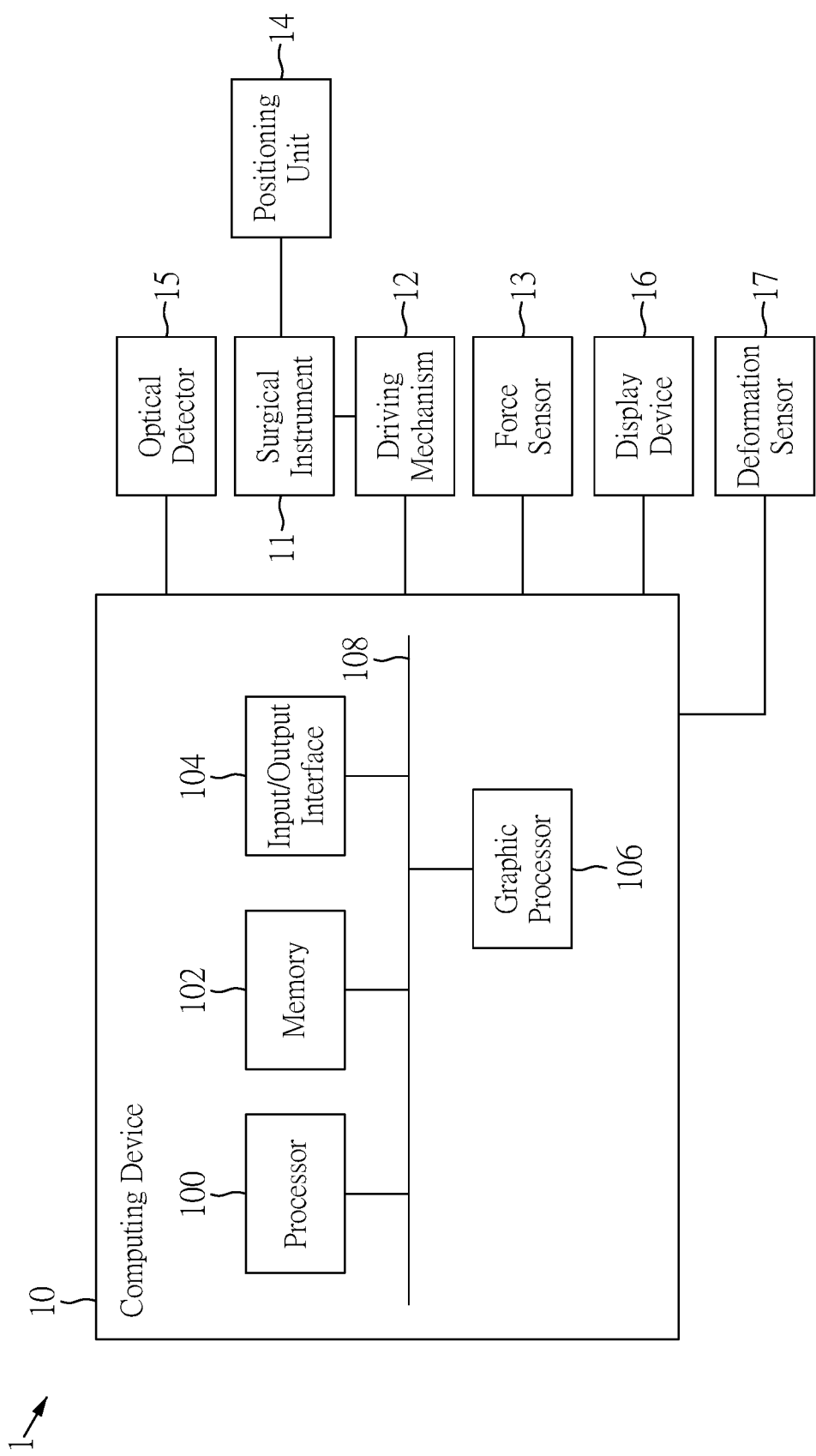
FIG. 1 is a functional block diagram of a navigation system for a surgical instrument according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

FIG. 1 is a functional block diagram of a navigation system for a surgical instrument according to one embodiment of the present disclosure. The embodiment of FIG. 1 provides a navigation system 1 including a computing device 10, a surgical instrument 11, a driving mechanism 12, a force sensor 13 and a deformation sensor 17.

The computing device 10 includes a processor 100, a memory 102, an input/output interface 104 and a graphic processor 106. The processor 100, the memory 102, the input/output interface 104 and the graphic processor 106 can communicate with each other through a bus 108, but the present disclosure is not limited thereto. The computing device 10 is implemented by, for example, a database, a general processor, a computer, a server, or other unique hardware device with a specific logic circuit or a device with a specific function, such as integrating program codes and a processor/chip into a unique hardware. In more detail, a part or all of the disclosed navigation system and navigation method can be implemented by using a computer program, and the computer program can be stored in a non-transitory computer-readable recording medium, such as a read-only memory, a flash memory, a floppy disk, a hard disk, an optical disk, a thumb drive, a magnetic tape, a database accessible through a network, or a computer-readable recording medium with the same function and known by those skilled in the art.

The processor 100 can be, for example, a programmable logic control circuit, a micro-processor circuit or an integrated circuit of a micro-control circuit, a central processing unit, and the like. The memory 102 is any storage device that can be used to store data, such as, but not limited to, random access memory (RAM), read only memory (ROM), flash memory, a hard disk or other storage device that can be used to store data. The graphic processor 106, also known as a display core, a visual processor, a display chip, a display card or a graphic chip, is a kind of microprocessor that performs graphics operations on personal computers, workstations, game consoles and some mobile devices (such as tablet computers, smart phones, etc.).

The input/output interface 104 can include one or more physical connection ports (for example, the input/output interface can be a general-purpose input/output or a connection port supporting HDMI, DisplayPort, USB, ethernet, EtherCAT (Ethernet for Control Automation Technology), etc.) and one or more wireless communication modules (such as wireless communication interface cards that support Bluetooth, WI-FI, etc.). The computing device 10 can be connected to the driving mechanism 12, the force sensor 13 and the deformation sensor 17 in a wired or wireless manner through the input/output interface 104.

Furthermore, the navigation system 1 can further include a positioning unit 14, an optical detector 15 and a display device 16. The computing device 10 can also be connected to the optical detector 15 and the display device 16 through the input/output interface 104 in a wired or wireless manner.

Figure 2:
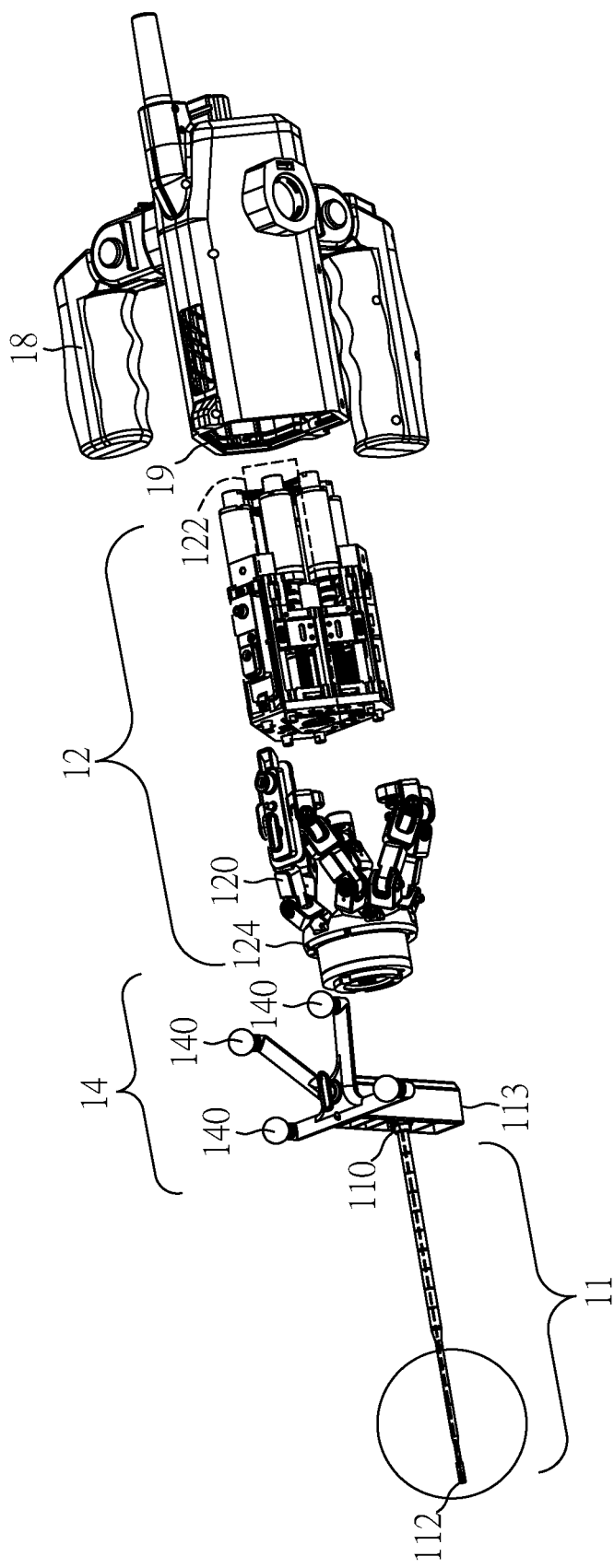
FIG. 2 is an exploded schematic diagram of a surgical instrument and a driving mechanism according to one embodiment of the present disclosure.
Figure 3:
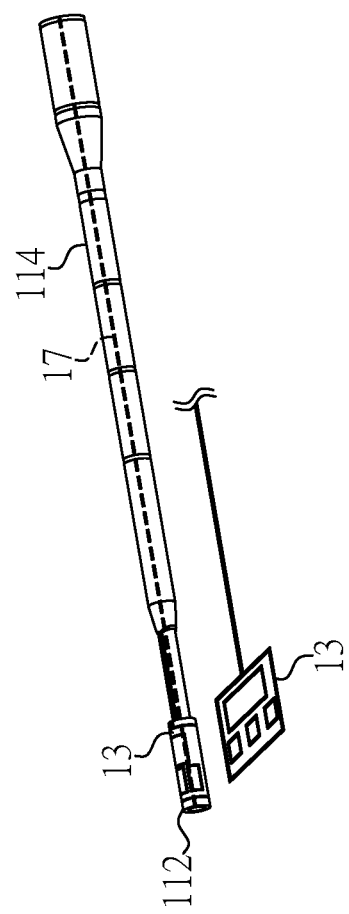
FIG. 3 is a partial enlarged view of a surgical instrument according to one embodiment of the present disclosure.

Referring to FIGS. 2 and 3, FIG. 2 is an exploded schematic diagram of a surgical instrument and a driving mechanism according to one embodiment of the present disclosure, and FIG. 3 is a partial enlarged view of a surgical instrument according to one embodiment of the present disclosure. As shown in FIGS. 2 and 3, the surgical instrument 11 can be, for example, a drill bit, a trocar or a saw blade, and is gripped by an adapter 113. The force sensor 13 electrically connected to the computing device 10 is disposed on the surgical instrument 11, and the surgical instrument 11 includes a main body 114 disposed between the transmission mechanism 110 and the operating end 112.

In some embodiments, the force sensor 13 can be in a sheet shape as shown in FIG. 3, and can be curled to enclose the main body 114 and is fixed adjacent to the operating end 112. Once the force sensor 13 completely covers a circumference of the operating end 112, the force sensor 13 can detect forces which come from all directions of the lateral of the operation end 112 and magnitudes of the forces. However, this embodiment is only an example, and an implementation manner of the force sensor 13 is not limited thereto. In other embodiments, the force sensor 13 can be disposed and fixed on the operating end 112 in a manner corresponding to surface topography of the surgical instrument 11. The deformation sensor 17 can be disposed on or inside the main body 114. For example, the deformation sensor 17 can be an optical fiber shape sensor disposed along the main body 114. By disposing a fiber Bragg grating (FBG) on the entire fiber, the computing device 10 can analyze variation of reflected light and provide accurate deformation measurement results by interpreting the information.

The drive mechanism 12 is connected to the transmission mechanism 110, and is controlled by the computing device 10 to drive the surgical instrument 11. In detail, the driving mechanism 12 utilizes a parallel mechanism with six degrees of freedom, in which six actuating units 122 and corresponding six groups of limbs 120 are incorporated.

Each actuation unit can include a motor, a coupling, a lead screw, and a slider. The motor can be electrically connected to the computing device 10, and when the computing device 10 controls the motor to drive the lead screw to rotate, the lead screw drives the limb 120. Through the above configuration, when the actuating unit 122 drives the limb 120, the movable plate 124 is moved or rotated to different positions/orientations in space, thereby moving the surgical instrument 11 on the adapter 113 to desired positions and orientations. The above-mentioned parallel mechanism utilizes a Stewart platform design known to those skilled in the art, and thus details thereof will not be repeated herein.

It should be noted that the force sensor 13 of the embodiment of the present disclosure is not connected to the transmission mechanism 110 of the surgical instrument 11 (that is, the force sensor 13 is not arranged at a front end of the Stewart platform), and the reasoning behind this configuration is that since force and torque fed back at the front end may be affected by a length of the instrument, deformation and noise, it is difficult for the computing device 10 to correctly analyze force components applied to the surgical instrument 11 along different directions, and a deviation, caused by the deformation due to applied forces, of the surgical instrument 11 cannot be compensated during navigation.

On the other hand, the driving mechanism 12 can be disposed in the housing 19 having one or more handles 18, allowing the user to hold the handles 18 and manipulate the surgical instrument 11 during operation. In addition, as to the type of the surgical instrument 11 to be used, one or more control buttons can be configured on the handle 18, such that the user can start, stop or adjust actions of the surgical instrument 11.

Figure 4:
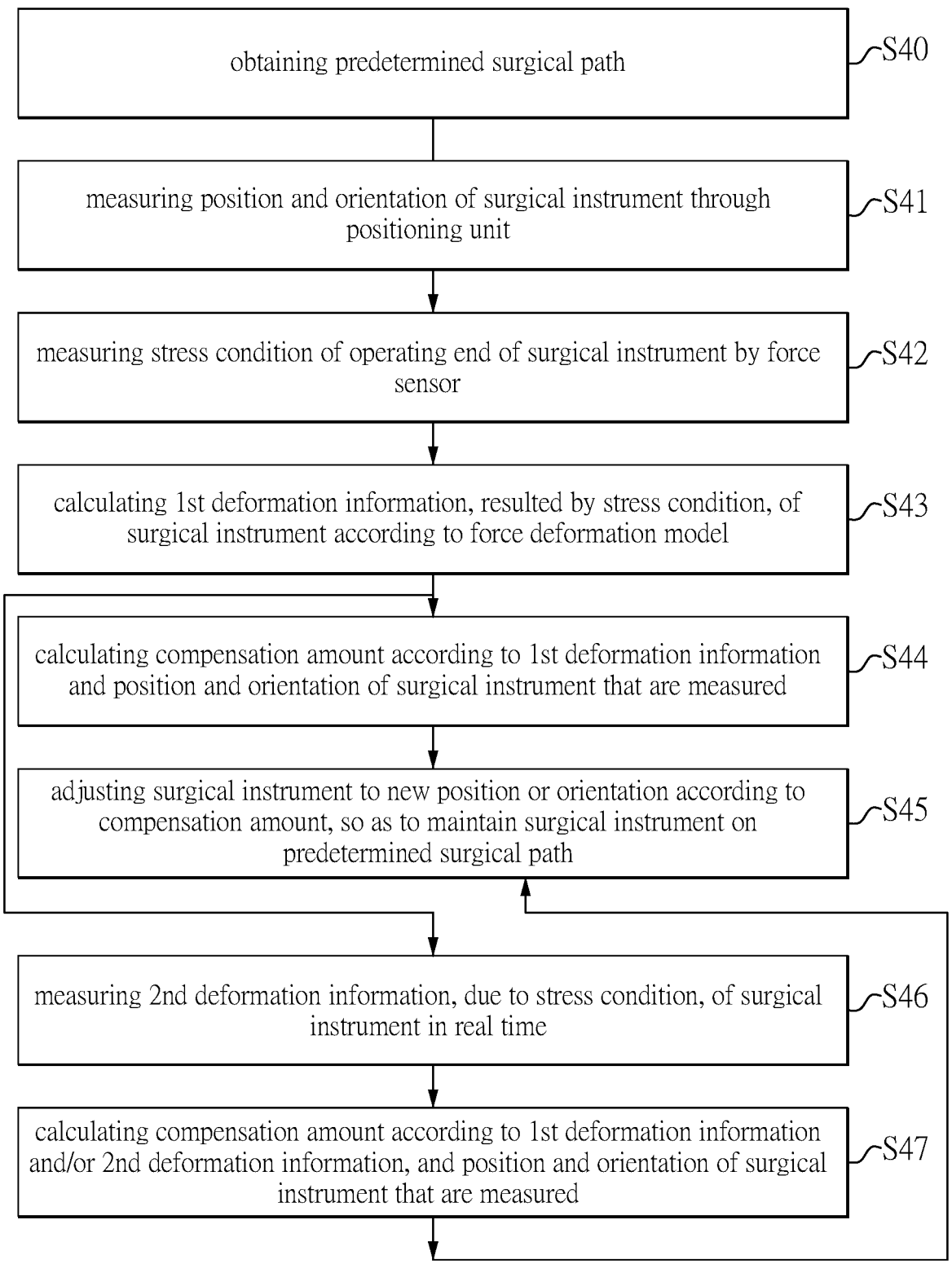
FIG. 4 is a flowchart of a navigation method for a surgical instrument according to one embodiment of the present disclosure.

The disclosed navigation method for the surgical instrument will be described based on FIG. 1 to FIG. 3 in the following. Reference is made to FIG. 4, which is a flowchart of a navigation method for a surgical instrument according to one embodiment of the present disclosure. It should be noted that in the embodiment of FIG. 4, the force sensor 13 is taken as a main component used to measure deformation information of the surgical instrument 11, and the deformation sensor 17 is used as an auxiliary component for determining the deformation information. However, in other embodiments, the deformation sensor 17 can also be adopted as the main component for measuring the deformation information of the surgical instrument 11, and the force sensor 13 is used as the auxiliary component for determining the deformation information. As shown in FIG. 4, the navigation method can be performed, by utilizing the computing device 10, the surgical instrument 11, the driving mechanism 12 and the force sensor 13 of the navigation system 1, and the navigation method comprises the following steps:

Step S40: obtaining a predetermined surgical path.

Figure 5:
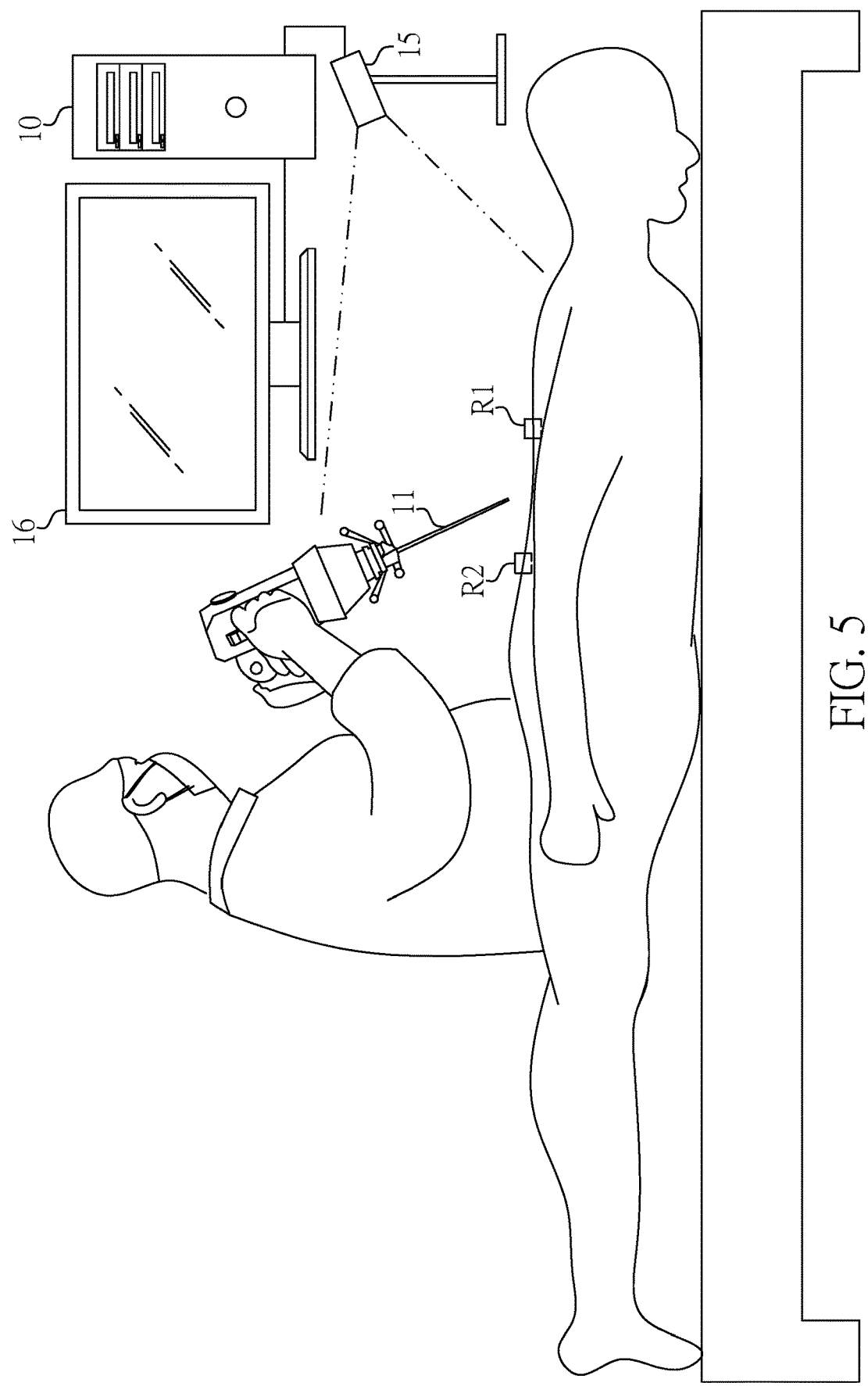
FIG. 5 is a schematic diagram of an orthopedic surgery being performed with a surgical instrument of the present disclosure according to one embodiment of the present disclosure.

Reference is made to FIG. 5, which is a schematic diagram of performing an orthopedic surgery with a surgical instrument of the present disclosure according to one embodiment of the present disclosure. As shown in FIG. 5, the surgical instrument 11 of the present disclosure is held by an operator to perform surgery on a patient's surgical site (e.g., a bone) according to a pre-planned surgical path. The computing device 11 can be configured to track a position and an orientation of the surgical instrument 11 by detecting positions of detection markers 140 through an optical detector 15. The detection markers 140 are provided as a part of an end-effector frame (EF) for navigation. In the present embodiment, the positioning unit 14 can further include a plurality of detection markers (not shown) disposed on the housing 19 to serve as a part of a robotic base frame (BF). The optical detector 15 detects positions of the BF and the EF, and the computing device 10 can calculate a distance between the two frames, and thus deduce a position of a tip of the surgical instrument 11.

Figure 6:
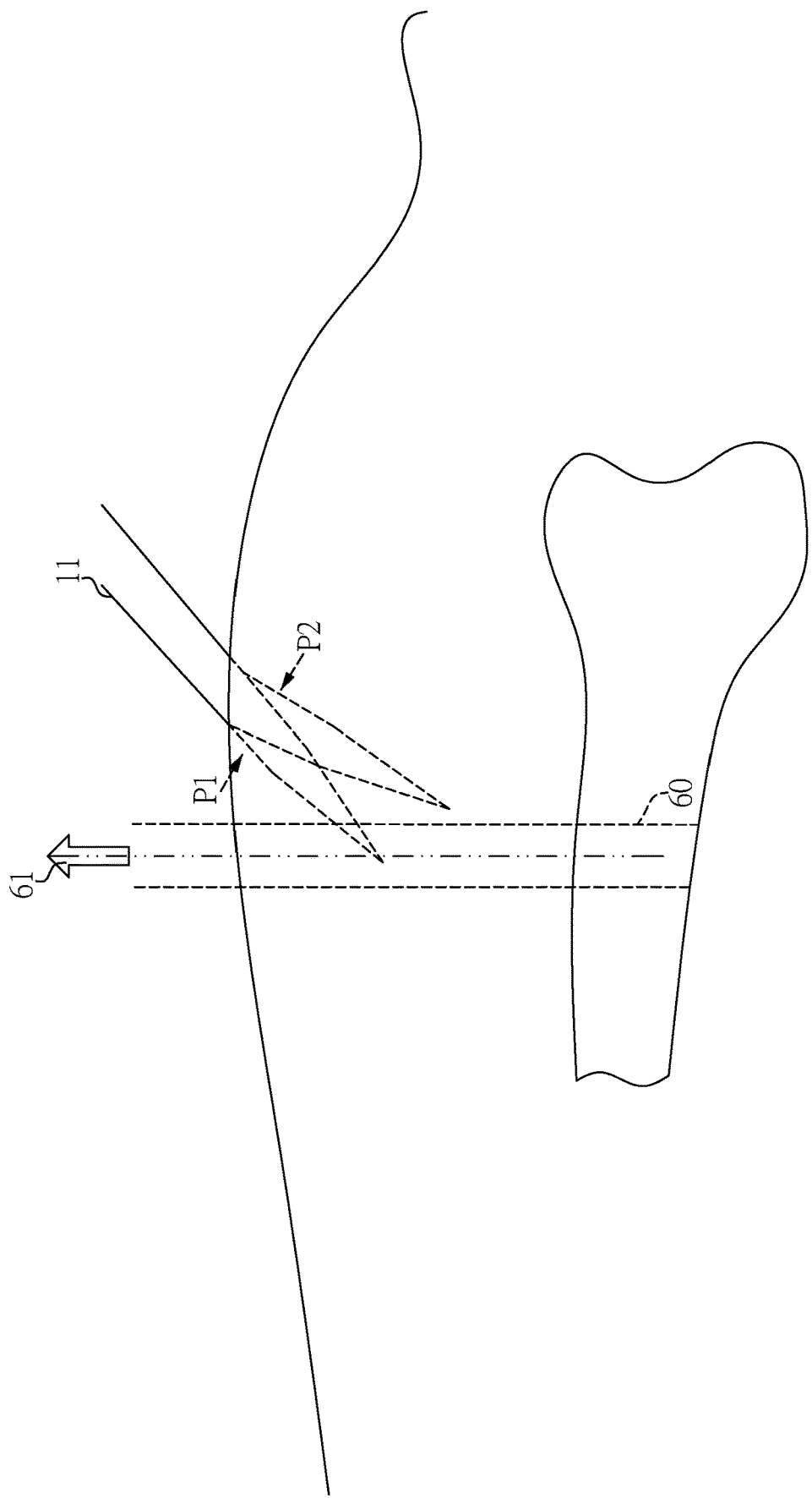
FIG. 6 is a schematic diagram showing a surgical site and a planned surgical path that are displayed on a navigation interface according to one embodiment of the present disclosure.

Reference is made to FIG. 6, which is a schematic diagram showing a surgical site and a planned surgical path that are displayed on a navigation interface according to one embodiment of the present disclosure. In more detail, after registering actual spatial coordinates to spatial coordinates containing a medical image of a surgical site, a spatial coordinate transformation matrix can be obtained. This spatial coordinate transformation matrix is based on dynamic reference frames R1 (or R2) near the surgical site, and transforms the actual spatial coordinates to the spatial coordinates of the medical image. During the surgery, the computing device 10 obtains, from the optical detector 15, coordinates of the dynamic reference frame R1 (or R2) near the surgical site and coordinates of the detection markers 140 adjacent to the surgical instrument 11. Actual spatial coordinates of the surgical instrument 11 can be transformed to spatial coordinates of the medical image through the above-mentioned spatial coordinate transformation matrix, and the surgical instrument 11 and the medical image of the surgical site are displayed on the navigation interface in real time.

In addition, the navigation interface can include multiple display windows for the user to view relative relationships between the surgical instrument 11 and the surgical site from multiple viewing angles (e.g., a top view, a side view, a front view and a perspective view), and in each window, the navigation system 1 updates the deformation information of the surgical instrument 11 in the window in real time according to the stress condition, details of which are illustrated hereinafter.

The user can then plan a to-be-performed surgical path 60 on a three-dimensional virtual anatomy displayed on the display device 16, e.g., a surgical path can be defined according to one or more pedicle screws to be implanted in the surgical site. In addition, when planning of the surgical path 60 is done, the computing device 10 can further calculate a virtual axis 61 extending to the epidermis of the surgical site according to the surgical path 60 and display the virtual axis 61 on the navigation interface, so as to indicate to the user where the location the surgery is to be performed. In this way, the user can stably manipulate the surgical instrument to move along the surgical path during the surgery.

Step S41: measuring a position and an orientation of the surgical instrument through a positioning unit.

Further referring to FIG. 2, the positioning unit 14 can be directly or indirectly connected to the surgical instrument 11, for example, the positioning unit 14 can be disposed on the adapter 113. The positioning unit 14 can assist in detecting the orientation and the position of the surgical instrument 11 relative to the surgical site through any existing tracking methods, such as optical tracking, electromagnetic tracking, or inertial tracking. In addition, the positioning unit 14 can, for example, include a plurality of markers for emitting electromagnetic signals, acoustic waves, heat or other sensible signals, and may be mounted on the adapter 113 in a specific direction and angle relative to the surgical instrument 11. In the embodiment of the present disclosure, an optical tracking method can be utilized, and therefore, the positioning unit 14 can include a plurality of detection markers 140. In one preferred embodiment of the present disclosure, the detection markers 140 are reflective balls disposed on the adapter 113 or marking devices that actively generate sensible signals. In addition, although not particularly shown, a plurality of detection markers can be disposed near the surgical site (for example, on the dynamic reference frames R1 and R2 implanted near the surgical site), so that the computing device 11 can detect the position and the orientation of the surgical instrument 11 relative to the surgical site through the optical detector 15.

Step S42: measuring a stress condition of the operating end of the surgical instrument by a force sensor. As previously described, the force sensor 13 can be disposed corresponding to the surface topography of the surgical instrument 11 and fixed on the operating end of the surgical instrument 11, so as to detect forces which comes from all directions of the lateral of the operating end 112, as well as magnitudes of the forces. In other embodiments, a bending condition of the operating end of the surgical instrument 11 can also be detected through the deformation sensor 17. The bending condition can be, for example, phase differences of reflected lights recorded at different positions.

Step S43: calculating first deformation information, resulted by the stress condition, of the surgical instrument according to a force deformation model. The deformation information is, for example, displacement lengths the surgical instrument 11 deviates from original axes at different positions. In other embodiments, it is also possible to calculate the first deformation information, caused by the bending condition, according to a force deformation model.

Figure 7:
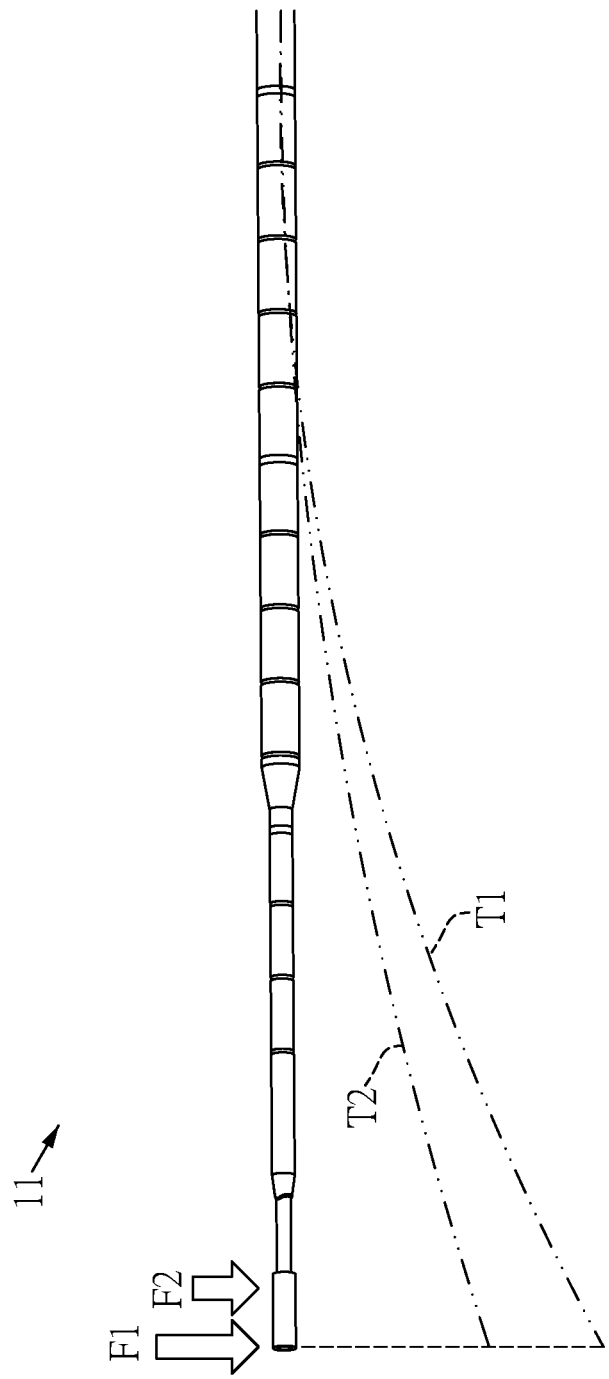
FIG. 7 is a schematic diagram of deformation information of a surgical instrument under different forces according to one embodiment of the present disclosure.

It should be noted that the force deformation model can, for example, be established by doing experiments on the surgical instrument 11 and recording deformation of the surgical instrument 11 under different force levels. Reference is made to FIG. 7, which is a schematic diagram of deformation information of a surgical instrument under different forces according to one embodiment of the present disclosure. As shown in FIG. 7, when a large external force F1 is applied to the operation end 112 of the surgical instrument 11, the surgical instrument 11 generates a trajectory T1 with a large deformation amount. On the contrary, when an external force F2 smaller than the external force F1 is applied to the operating end 112 of the instrument 11, the surgical instrument 11 generates a trajectory T2 with a small amount of deformation. Similarly, in other embodiments, the force deformation model can be established by, for example, performing experiments on the surgical instrument 11 and recording phase differences of reflected lights at different positions and the deformation information at the different positions.

Therefore, for different magnitudes and positions of applied external forces, or the phase differences of reflected lights at different positions, repetitive experiments can be done and deformation information may be recorded, thus the force deformation model can be established and stored in the memory 102. The computing device 10 can calculate, according to the force deformation model, the first deformation information when the force sensor 13 detects forces, as well as magnitudes of the forces, from all directions of the lateral of the operating end 112. Alternatively, the computing device 10 can calculate, according to the force deformation model, the first deformation information when the deformation sensor 17 detects the bending condition of the operating end 112. As the surgical instrument 11 goes deeper, deformation of the surgical instrument 11 may not be visible, and the calculated first deformation information can assist in correcting the position and the orientation of the surgical instrument 11 as displayed on the navigation interface in subsequent steps.

Figure 8:
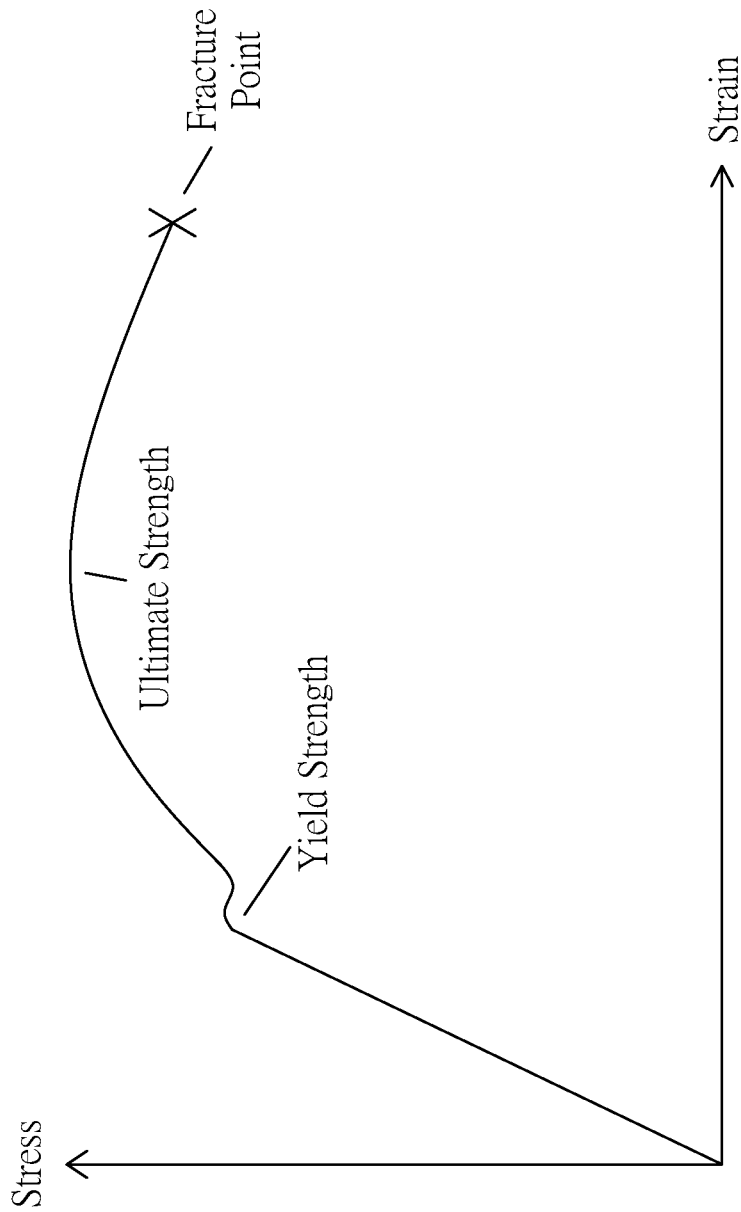
FIG. 8 is a graph showing a strain-stress curve of a surgical instrument according to one embodiment of the present disclosure.

In addition, in some embodiments, the force deformation model can also define strain-stress relationship of the surgical instrument 11. Reference is made to FIG. 8, which is a graph showing a strain-stress curve of a surgical instrument according to one embodiment of the present disclosure. As shown in FIG. 8, a linear elastic region, a strain hardening region and a necking region of the surgical instrument 11 are respectively separated by the yield strength, ultimate strength of the surgical instrument 11, and the stress condition under which the surgical instrument 11 will fracture. In terms of the curve, a cautionary force range can be designed for warning the user that the surgical instrument 11 may be damaged. In other words, if forces applied on the surgical instrument 11 exceed the set force range or the surgical instrument 11 deviates by a certain displacement length, the display device 16 can remind the user that there is a risk of instrument breakage, or the computing device 10 can execute a corresponding risk control program, for example, to mandatorily stop the surgical instrument 11 and prevent vital organs from being injured. In one exemplary embodiment of the present disclosure, the warning force range can be, for example, between the yield strength and the ultimate strength of the surgical instrument, and the force range that triggers the mandatory stop can be, for example, a region between the ultimate strength and the fracture point, but the present disclosure is not limited thereto.

Step S44: calculating a compensation amount according to the first deformation information and the position and the orientation of the surgical instrument that are measured.

Further referring to FIG. 6, which shows position and orientation information P1 of the surgical instrument 11 that does not take into account the deformation information (which can be displayed in the navigation interface) and position and orientation information P2 of the surgical instrument 11 that takes into account the deformation information (which may not be displayed in the navigation interface). In a general case where the deformation information is not taken into account, as the surgical instrument 11 penetrates deep into the surgical site, the orientation and the position of the surgical instrument 11 relative to the surgical site can only be detected through the detection markers 140, and the computing device 10 can only predict and display the position and orientation information P1 of the surgical instrument 11 in the navigation interface, which may make the user mistakenly believe that actual position of the surgical instrument 11 is as displayed by P1.

However, after taking into account the deformation information of the operating end 112 of the surgical instrument 11, the deviation of the surgical instrument 11 can be obtained, and the deviation can be used as a compensation amount. For example, the tip of the position and orientation information P1 that does not take the deformation of the surgical instrument 11 into account is used as a reference point, the tip of the position and orientation information P2 (not shown in the navigation interface) that does take the deformation of the surgical instrument 11 into account is used as another reference point, and a shift distance and an angle between the tips of P1 and P2 can be used as the compensation amount. In detail, the calculated deviation of the surgical instrument 11 can include a topographic change, a positional change, and an orientation change of the surgical instrument 11.

Step S45: adjusting the surgical instrument to a new position or orientation according to the compensation amount, so as to maintain the surgical instrument on the predetermined surgical path.

In some embodiments of the present disclosure, there are several ways to apply the compensation amount. For example, in the three-dimensional virtual environment, the position and orientation information P1 can be directly corrected according to the compensation amount. Alternatively, in the three-dimensional virtual environment, the orientation and the position of the surgical site relative to the surgical instrument 11 can be corrected according to the compensation amount. A third way is to directly move the driving mechanism 12 according to the compensation amount without modifying the information on the display interface, such that the position and the orientation of the surgical instrument 11 relative to the surgical site in the real space are consistent with information provided in the navigation interface of the display device 16. Therefore, the method of applying the compensation amount can be adjusted according to a type of the surgical instrument 11 or the amount of computation required by the computing device 10, and the present disclosure does not limit the method to be utilized.

For the above-mentioned third method for applying the compensation amount, after the position and orientation information P2 is obtained through performing correction, the computing device 10 can further control orientation and position of the surgical instrument 11 in the real space by the plurality of limbs 120 that are respectively connected to the plurality of actuating units 122, thereby assisting the user in stably manipulating the surgical instrument 11 to move along the surgical path 60 during the surgery.

Reference is further made to FIGS. 1 to 3. In some embodiments, the navigation system 1 can also utilize the deformation sensor 17. The deformation sensor 17 can be, for example, a curve sensor, and its working principles include measuring local curvature lengthways and converting the measurement into a shape of the curve. The curve sensor includes two strips connected at one end. When laid flat, electrodes in the curve sensor are arranged in a specific way, but when the curve sensor is bent, arrangement of the electrodes changes due to different radius curves. This change is a direct measurement of curvature. A detailed model of the curve can be obtained from numerous displacement measurements taken at various position along the strips.

In some embodiments, the deformation sensor 17 can also be a flexible sensor strip using a metal foil, which can perform directional measurement of bending. The flexible sensor strip includes a plurality of strain sensors arranged along a strip body, and a shape of the strip body can be reconstructed by integrating data of the strain sensors through execution of an algorithm.

In addition to being disposed along the main body 114 as shown in FIGS. 2 and 3, similar to the force sensor 13, the deformation sensor 17 can also enclose the surface of the operating end of the surgical instrument 11 and can obtain the second deformation information.

Therefore, as shown in FIG. 4, the navigation method further includes the following steps:

Step S46: measuring the second deformation information, due to the stress condition, of the surgical instrument in real time.

Step S47: calculating the compensation amount according to the first deformation information and/or the second deformation information, and the position and the orientation of the surgical instrument that are measured. The navigation method then returns to step S45 to adjust the surgical instrument to a new position or orientation according to the compensation amount, so as to maintain the surgical instrument on the predetermined surgical path.

In other words, in the present embodiment, when the force sensor 13 and the deformation sensor 17 are used at the same time, according to practical requirements, the user can choose to use one of the first deformation information and the second deformation information to obtain the deformation information, or the user can choose to use both of the first and second deformation information at the same time to further improve the accuracy of the operation.

Beneficial Effects of the Embodiments

In conclusion, one of advantages of the disclosure is that, in the disclosed navigation method and the navigation system for the surgical instrument, the deformation information of the surgical instrument can be measured and calculated in real time, the deviation of the surgical instrument can be calculated and corrected according to the deformation information during navigation. Also, the deviation of the surgical instrument can be displayed on a navigation interface and correspondingly compensated in real time, which can improve an overall navigation accuracy.

In addition, in the disclosed navigation method and navigation system for the surgical instrument, force and temperature conditions of the surgical instrument can be monitored in real time during the navigation, and if the exerted force exceeds a set range, the user is reminded of potential breakage of the surgical instrument, or a corresponding risk control process is executed.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A navigation method for a surgical instrument, comprising:
    setting a predetermined surgical path;
    measuring a position and an orientation of the surgical instrument through a positioning unit, wherein the surgical instrument has a transmission mechanism and an operating end;
    measuring a stress condition or a bending condition of the operating end of the surgical instrument by a sensor;
    calculating first deformation information, resulted by the stress condition, of the surgical instrument according to a force deformation model;
    calculating a compensation amount according to the first deformation information, the position and the orientation of the surgical instrument; and
    adjusting the surgical instrument to a new position or a new orientation according to the compensation amount, so as to maintain the surgical instrument on the predetermined surgical path.

2. The navigation method according to claim 1, wherein the positioning unit includes a plurality of detection markers, and the navigation method further comprises: detecting positions of the detection markers by an optical detector to track the position and the orientation of the surgical instrument.

3. The navigation method according to claim 1, further comprising: adjusting, by a plurality of limbs that are respectively connected to a plurality of actuating units, the surgical instrument to the new position or orientation according to the compensation amount.

4. The navigation method according to claim 1, further comprising: displaying the first deformation information on a navigation interface for navigating the surgical instrument.

5. The navigation method according to claim 1, wherein the surgical instrument includes a main body disposed between the transmission mechanism and the operation end.

6. The navigation method according to claim 5, wherein the force deformation model defines a strain-stress curve of the main body of the surgical instrument.

7. The navigation method according to claim 5, wherein the sensor is a sheet-shaped force sensor which encloses the main body and is fixed adjacent to the operating end.

8. The navigation method according to claim 5, wherein the sensor is an optical fiber shape sensor disposed along the main body.

9. A navigation system, comprising:
a computing device including a processor and a memory;
a surgical instrument, wherein a sensor electrically connected to the computing device is disposed on the surgical instrument, and the surgical instrument has a transmission mechanism and an operating end; and
a driving mechanism connected to the transmission mechanism and controlled by the computing device to drive the surgical instrument;
wherein the processor is configured to:
obtain a predetermined surgical path;
measure a position and an orientation of the surgical instrument through a positioning unit;
measure a stress condition or a bending condition of the operating end of the surgical instrument by a sensor;
calculate first deformation information, resulted by the stress condition, of the surgical instrument according to a force deformation model;
calculate a compensation amount according to the first deformation information and the position and the orientation of the surgical instrument that are measured; and
adjust the surgical instrument to a new position or a new orientation according to the compensation amount, so as to maintain the surgical instrument on the predetermined surgical path.

10. The navigation system according to claim 9, wherein the positioning unit includes a plurality of detection markers, and the computing device is further configured to track the position and the orientation of the surgical instrument by detecting positions of the detection markers through an optical detector.

11. The navigation system according to claim 9, further comprising a plurality of limbs that are respectively connected to a plurality of actuating units, wherein the surgical instrument is adjusted to the new position or the new orientation by the limbs according to the compensation amount.

12. The navigation system according to claim 9, further comprising a navigation interface electrically connected to the computing device for navigating the surgical instrument and displaying the first deformation information.

13. The navigation system according to claim 9, wherein the surgical instrument includes a main body disposed between the transmission mechanism and the operation end.

14. The navigation system according to claim 13, wherein the force deformation model defines a strain-stress curve of the main body.

15. The navigation system according to claim 13, wherein the sensor is a sheet-shaped force sensor which encloses the main body and is fixed adjacent to the operating end.

16. The navigation system according to claim 13, wherein the sensor is an optical fiber shape sensor disposed along the main body.

* * * * *